United States Patent [19]
Mita et al.

[11] Patent Number: 4,552,765
[45] Date of Patent: Nov. 12, 1985

[54] ALETHEINE DERIVATIVES

[75] Inventors: Itaru Mita, Ashiya; Jun-ichi Iwao, Takarazuka; Tadashi Iso, Sakai; Masayuki Oya, Ibaraki, all of Japan

[73] Assignee: Santen Pharmaceutical Co., Ltd., Osaka, Japan

[21] Appl. No.: 488,100

[22] Filed: Apr. 25, 1983

[30] Foreign Application Priority Data

May 14, 1982 [JP] Japan ................................. 57-82155
Oct. 20, 1982 [JP] Japan ................................ 57-185026
Nov. 15, 1982 [JP] Japan ................................ 57-200934

[51] Int. Cl.$^4$ .......................................... C07C 103/127
[52] U.S. Cl. .................................... 514/513; 564/154
[58] Field of Search ........................ 564/154; 424/324

[56] References Cited
U.S. PATENT DOCUMENTS 4,216,160  8/1980  Dorn et al. ..................... 564/154 X
4,240,823 12/1980  Clapot et al. .................. 564/154 X
4,251,459  2/1981  Bargeron et al. ............... 564/154 X

OTHER PUBLICATIONS

Journal of American Chemical Society, vol. 75, Tsoo E. King et al, pp. 1290–1292, (1953).
Journal of American Chemical Society, vol. 75, E. L. Wittle et al, pp. 1694–1700, (1953).
Journal of American Chemical Society, J. Baddiley et al, pp. 800–803, (1952).

*Primary Examiner*—Paul F. Shaver
*Attorney, Agent, or Firm*—Frishauf, Holtz, Goodman & Woodward

[57] ABSTRACT

Aletheine derivatives of the general formula

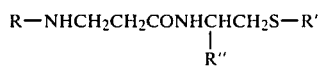

which are useful for treatment of liver damage.

15 Claims, No Drawings

ALETHEINE DERIVATIVES

BACKGROUND OF THE INVENTION

N-β-Alanyl-2-mercaptoethylamine (hereinafter referrs to as β-aletheine) is well known as the constituent of pantetheine and pantethine. Pantetheine or pantethine, when administered to human, is rapidly converted into coenzyme-A which plays an important role in lipo-metabolism. β-Aletheine forms the terminal structure of coenzyme-A, but useful pharmacological effects thereof has not been known. The utilization of β-aletheine, as an intermediate for preparing pantetheine or pantethine is only reported (*Journal of American Chemical Society*, 75, 1290 (1953), ibid., 75, 1695 (1953), *Journal of Chemical Society*, 1952, 800). As the result of our precise examination on the pharmacological effects of β-aletheine, we found that β-aletheine itself shows an excellent suppressive effect on liver damage. We continuously studied the known aletheine derivatives and found that N,S-diacetyl derivative and N-benzyloxycarbonyl derivative have a superior effect on liver-damage.

On the other hand, through further studies on for β-aletheine we prepared novel β-aletheine derivatives and examined their pharmacological effects and found that they also have superior effect on liver damage.

DETAILED DESCRIPTION OF THE INVENTION

This invention relates to novel β-aletheine derivatives of the formula [I] and salts thereof, $$R^1-NHCH_2CH_2CONHCHCH_2S-R^3 \quad [I]$$
$$\underset{R^2}{|}$$

wherein
$R^1$ is

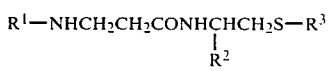

$R^2$ is hydrogen or carboxy;
$R^3$ is lower alkanoyl, (lower alkylamino)thiocarbonyl or

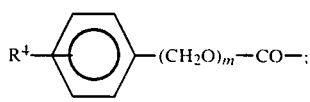

$R^4$ is hydrogen, lower alkyl or lower alkoxy; and
m and n, same or differnt, each is 0 or 1,
the same shall be applied hereinafter,
and the use for suppressive agent of liver damage comprising the compounds of the formula [II], $$R^5-NHCH_2CH_2CONHCHCH_2S-R^7 \quad [II]$$
$$\underset{R^6}{|}$$

wherein
$R^5$ is hydrogen, lower alkanoyl or

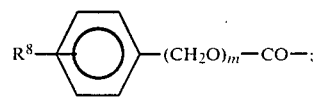

$R^6$ is hydrogen or carboxy;
$R^7$ is hydrogen, lower alkanoyl, (lower alkylamino)thiocarbonyl or

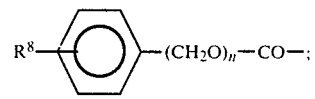

$R^8$ is hydrogen, lower alkyl or lower alkoxy; and
m and n, same or different, each is 0 or 1,
the same shall be applied hereinafter.

In the formulas, lower alkyl represents the groups having 1 to 6 carbon atoms exemplified by methyl, ethyl, propyl or hexyl, lower alkoxy represents the groups having 1 to 6 carbon atoms exemplified by methoxy, ethoxy, propoxy or hexyloxy, and lower alkanoyl represents the groups having 2 to 6 carbon atoms exemplified by acetyl, propionyl, pivaloyl or hexanoyl.

In the compounds represented by the formula [II], β-aletheine (in the formula, $R^5$, $R^6$ and $R^7$ each is hydrogen), N,S-diacetyl-β-aletheine (in the formula, $R^5$ and $R^7$ each is acetyl, and $R^6$ is hydrogen) and N-benzyloxycarbonyl-β-aletheine (in the formula, $R^5$ is benzyloxycarbonyl, and $R^6$ and $R^7$ each is hydrogen) are known compounds. But, their useful pharmacological effects have not been known. As the result of our precise examination on the pharmacological effects on β-aletheine derivatives, we found that not only novel β-aletheine derivatives (formula [I]) but also the known β-aletheine derivatives show an excellent suppresive effect on liver damage.

Novel β-aletheine derivatives represented by the formula [I] can be prepared, for example, by the following methods.

(a) Reaction of the compound of the formula [III] with the compound of the formula [IV] or active derivatives thereof (acid anhydride, mixed anhydride, etc.), $$R^9-NHCH_2CH_2CONHCHCH_2SH +$$
$$\underset{R^2}{|}$$
$$[III]$$

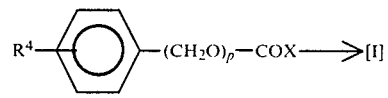

[IV]

wherein
$R^9$ is hydrogen or

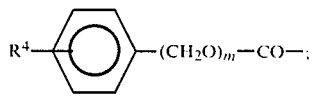

X is halogen or hydroxy; and
p is m or n, the same shall be applied hereinafter.

(b) Reaction of the compound of the formula [V] with the compound of the formula [VI] or active derivatives thereof (acid anhydride, mixed anhydride, etc.).

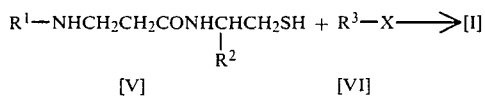

(c) Reaction of the compound of the formula [VII] with the compound of the formula [VIII],

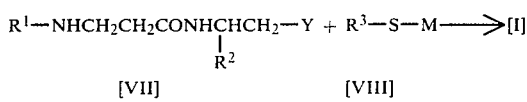

wherein
Y is halogen; and
M is alkali metal.

The known β-aletheine derivatives, namly β-aletheine, N,S-diacetyl-β-aletheine and N-benzyloxycarbonyl-β-aletheine, were prepared according to the literature (*Journal of American Chemical Society*, 75, 1290 (1953) and *Journal of Chemical Society*, 1952, 800).

The compounds of the invention can be converted to the pharmaceutically acceptable salts, for example, sodium salt, calcium salt, alminium salt, ammonium salt, diethylamine salt, triethanolamine salt, hydrochloric acid salt or sulfuric acid salt.

In the case of the existence of asymmetric carbon atoms (for example, in the formula [I], $R^2$ is represented by carboxy), the compounds of the invention have stereoisomers, and these isomers are included in this invention.

Following pharmacological study proved that β-aletheine derivatives of this invention have superior effect on liver damage.

PHARMACOLOGICAL STUDY

Generally, the effect of a certain compound on liver damage is examined by administering it to experimental animals before a liver damage inducer such as carbon tetrachloride, thioacetamide, bromobenzene, paracetamol, D-galactosamine, etc. Carbon tetrachloride ($CCl_4$)-induced liver damage is commonly used as the model. The mechanism to induce liver damage is presumed as follows (*Biochemical Pharmacology* 21, 49 (1972), ibid., 25, 2163 (1976)).

The cleavage of carbon-chlorine bond of $CCl_4$ by cytochrome p-450 in liver produces highly toxic free radical ($CCl_3$.). The free radical is bound to thiol group of protein or accelerates lipo-peroxidation of cell membrane to cause liver damage.

In this invention, the effect of the compounds were examined against $CCl_4$-induced liver damage using serum transaminase activities (s-GOT and s-GPT) as a parameter.

Experimental method

Male wistar rats (6 animals per group), weighing about 170-200 g, fasted for 17 hours, were used in the experiments. Test compounds were given orally at a dose of 300 mg/Kg, and 60 minutes later $CCl_4$ was administered intraperitoneally at a dose of 0.25 ml/Kg (5 ml/Kg as a 5%(v/v)solution in olive oil).

As the control, olive oil only was given intraperitoneally at a dose of 5 ml/Kg. All animals were killed 24 hours after $CCl_4$ administration and their s-GOT and s-GPT activities were determined.

Results of pharmacological tests are shown in the Tables I and II. As shown in the Tables, the compounds of the invention significantly suppressed the $CCl_4$-induced elevation of s-GOT and s-GPT activities when compared with the case of control group.

TABLE I

| | serum transaminase | |
|---|---|---|
| compound No. | s-GOT Karmen unit/ml (inhibitory %) | s-GPT Karmen unit/ml (inhibitory %) |
| control | 11460 ± 1490 | 5100 ± 405 |
| compound No. 1 | 5250 ± 1330 (54%) | 2590 ± 731 (49%) |
| compound No. 2 | 3550 ± 1150 (69%) | 1720 ± 613 (66%) |
| compound No. 3 | 6150 ± 2990 (46%) | 2440 ± 960 (52%) |

Each value represents a mean value ± standard deviation (6 animals/group).
compound No. 1: N—(2-acetylthioethyl)-3-(benzyloxycarbonylamino)propionamide[S—acetyl-N—benzyloxycarbonyl-β-aletheine]
compound No. 2: 3-(benzyloxycarbonylamino)-N—(2-propionylthioethyl)propionamide[N—benzyloxycarbonyl-S—propionyl-β-aletheine]
compound No. 3: 3-benzoylamino-N—(2-benzoylthioethyl)propionamide[N,S—dibenzoyl-β-aletheine]

TABLE II

| | serum transaminase | |
|---|---|---|
| compound No. | s-GOT Karmen unit/ml (inhibitory %) | s-GPT Karmen unit/ml (inhibitory %) |
| control | 13950 ± 4030 | 6400 ± 2590 |
| compound No. 4 | 4690 ± 2490 (67%) | 1990 ± 1010 (69%) |
| compound No. 5 | 4450 ± 4430 (69%) | 1900 ± 1640 (71%) |
| compound No. 6 | 3370 ± 1360 (76%) | 1730 ± 800 (73%) |

Each value represents a mean value ± standard deviation (6 animals/group).
compound No. 4: 3-amino-N—(2-mercaptoethyl)propionamide hydrochloride[β-aletheine hydrochloride]
compound No. 5: 3-(benzyloxycarbonylamino)-N—(2-mercaptoethyl)propionamide[N—benzyloxycarbonyl-β-aletheine]
compound No. 6: 3-acetylamino-N—(2-acetylthioethyl)propionamide[N,S—diacetyl-β-aletheine]

TOXICITY TEST (animal)

Male ddY-SPF strain mice (4 weeks of age, weighing 19-21 g) were placed in a breeding room of constant temperature and huminity (23±1° C., 55±5%) and fed freely pellet diet and water ad. libitum for a week. Mice showing normal growth were selected for the test.

(method of administration)

Test compound is suspended in 0.5% tragacanth suspension and administered orally.

(result)

$LD_{50}$(mg/Kg) values of the test compounds (compound No.1-6) were over 1000 mg/Kg.

The compounds of the invention can be administered either orally or parenterally. The dose is adjusted depending on symptom, dosage form, etc., but usual daily dosage for adult is 10–3000 mg, preferably 300–900 mg, for oral administration.

The dosage forms are tablet, granule, powder, capsule, etc. Usual additives such as binder (ethyl cellulose, polyvinylpyrrolidone, etc.), diluent (lactose, crystalline cellulose, etc.), disintegrator (calcium carboxymethylcellulose etc.), lubricant (talc, colloidal silica, etc.) etc. can be used for the formulations.

Examples of the formulations are shown below.

| (a) Tablet | |
|---|---|
| compound No. 2 | 100 mg |
| ethyl cellulose | 50 mg |
| crystalline cellulose | 80 mg |
| calcium carboxymethylcellulose | 7 mg |
| magnesium stearate | 3 mg |
| Total | 240 mg |
| compound No. 4 | 100 mg |
| ethyl cellulose | 50 mg |
| crystalline cellulose | 80 mg |
| calcium carboxymethylcellulose | 7 mg |
| magnesium stearate | 3 mg |
| Total | 240 mg |
| compound No. 6 | 100 mg |
| ethyl cellulose | 50 mg |
| crystalline cellulose | 80 mg |
| calcium carboxymethylcellulose | 7 mg |
| magnesium stearate | 3 mg |
| Total | 240 mg |

The tablets may be treated with the common film-coating and further with sugar-coating.

| (b) Granule | |
|---|---|
| compound No. 6 | 100 mg |
| polyvinylpyrrolidone | 25 mg |
| lactose | 365 mg |
| talc | 10 mg |
| Total | 500 mg |
| (c) Powder | |
| compound No. 6 | 200 mg |
| lactose | 450 mg |
| starch | 320 mg |
| colloidal silica | 30 mg |
| Total | 1000 mg |
| (d) Capsule | |
| compound No. 6 | 100 mg |
| lactose | 32 mg |
| crystalline cellulose | 56 mg |
| colloidal silica | 2 mg |
| Total | 190 mg |

EXAMPLE 1

3-(Benzyloxycarbonylamino)-N-[2-(benzyloxycarbonylthio)-ethyl]propionamide

To the stirred solution of 3-amino-N-(2-mercaptoethyl)propionamide hydrochloride (9.0 g) in 4N sodium hydroxide solution (12.3 ml) benzyloxycarbonyl chloride (16.7 g) and 4N sodium hydroxide solution (24.6 ml) are dropped simultaneously under ice-water cooling. After the addition, the mixture is stirred for 30 minutes under ice-water cooling and further 30 minutes at room temperature. The reaction mixture is extracted with ethyl acetate and the organic layer is washed with hydrochloric acid, water and then saturated sodium chloride solution. The solution is dried over anhydrous magensium sulfate and concentrated in vacuo to give 15 g (74%) of the titled compound.

mp 121°–122° C. (ethy acetate)

IR (KBr, cm$^{-1}$): 3315, 3290, 1708, 1682, 1642, 1542, 1536, 1268, 1248, 1140, 742, 696

NMR (CDCl$_3$, δ)

2.14–2.53 (2H, m, —NCH$_2$CH$_2$CO—), 2.81–3.16 (2H, m,

—NCH$_2$CH$_2$SCO—), 3.44 (4H, q, J = 5.6 Hz,

—NCH$_2$CH$_2$CO— and —NCH$_2$CH$_2$SCO—), 5.04 and 5.17 (4H, each s, 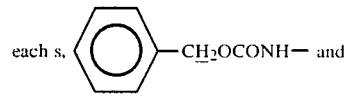

CH$_2$OCOS—), 5.33–5.83 (1H, br, —CONH—), 6.13–6.56 (1H, br, —CONH—), 7.27 and 7.30
(10H, each s, aromatic H)

TLC Rf value$^{(a)}$: 0.43

(a): silica gel, benzene-ethyl acetate-acetic acid (25:25:1)

EXAMPLE 2

3-Benzoylamino-N-(2-benzoylthioethyl)propionamide

To the stirred solution of 3-amino-N-(2-mercaptoethyl)propionamide hydrochloride (5.0 g) in 4N sodium hydroxide solution (6.8 ml), benzoyl chloride (7.6 g) and 4N sodium hydroxide solution (13.5 ml) are simultaneously dropped under ice-water cooling and proceeded as directed in Example 1.

8.8 g (91%) of the titled compound is obtained.

mp 154°–155° C. (water—ethanol)

IR (KBr, cm$^{-1}$): 3305, 1657, 1640, 1632, 1538, 1204, 915, 690

NMR (DMSO—d$_6$, δ)

2.44 (2H, t, J = 7.0 Hz, —NCH$_2$CH$_2$CO—), 2.98–3.77 (6H, m,

—NCH$_2$CH$_2$CONHCH$_2$CH$_2$S—), 7.27–8.01 (10H, m, aromatic H), 8.14 (1H, t, J = 5.0 Hz, —CONH—), -continued
8.41 (1H, t, J = 6.0 Hz, —CONH—)

TLC Rf value(b): 0.53
(b): silica gel, ethyl acetate-chloroform-acetic acid (7:5:1)

Following compounds are prepared by the similar method as in Example 2.

3-[(4-methoxy)benzyloxycarbonylamino]-N-[2-[(4-methoxy)-benzyloxycabonylthio]ethyl]propionamide Yield 83%
mp 142.5°–144° C. (methanol)
IR (KBr, cm$^{-1}$): 3345, 3300, 1700, 1682, 1644, 1539, 1527, 1240, 1146

NMR (CDCl$_3$, δ)
2.31 (2H, t, J = 6.0 Hz, —NHCH$_2$CH$_2$CO—), 2.95 (2H, t, J = 6.0 Hz, —NHCH$_2$CH$_2$SCO—), 3.42 (4H, m, —NHCH$_2$CH$_2$CONHCH$_2$CH$_2$S—), 3.75 (6H, s, —OCH$_3$ × 2),

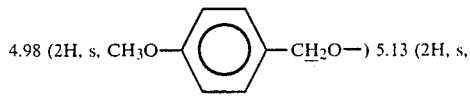 4.98 (2H, s, CH$_3$O—⟨❍⟩—CH$_2$O—) 5.13 (2H, s,

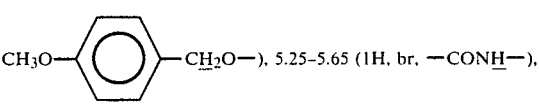 CH$_3$O—⟨❍⟩—CH$_2$O—), 5.25–5.65 (1H, br, —CONH—), 5.99–6.47 (1H, br, —CONH—), 6.81 (4H, d, J = 8.0 Hz,

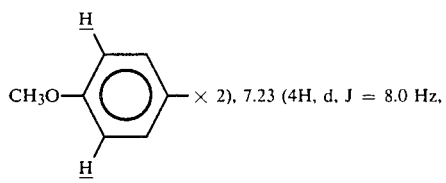 CH$_3$O—⟨❍⟩—× 2), 7.23 (4H, d, J = 8.0 Hz,

CH$_3$O—⟨❍⟩—× 2)

TLC Rf value: 0.31(a), 0.67(b)
3-[(4-Methyl)benzyloxycarbonylamino]-N-[2-[(4-methyl)benzyloxycarbonylthio]ethy]propionamide

EXAMPLE 3

3-(Benzyloxycarbonylamino)-N-[2-(benzoylthio)ethyl]-propionamide

To the solution of 3-(benzyloxycarbonylamino)-N-(2-bromoethyl)propionamide (10.0 g, 0.03 mol) in acetone (250 ml), acetone (100 ml) solution of potassium thiobenzoate (5.35 g, 0.03 mol) is added. The mixture is stirred for 1 hour and insoluble substance is filtered off. The filtrate is concentrated in vacuo and the residue is dissolved in chloroform. The solution is washed with sodium hydroxide solution, water and then saturated sodium chloride solution, and dried over anhydrous magnesium sulfate. The solution is concentrated in vacuo to give 7.9 g (68%) of the titled compound.
mp 115°–118° C. (ethyl acetate)

IR (KBr, cm$^{-1}$): 3320, 1688, 1658, 1648, 1544, 1268, 1202, 914, 693

NMR (CDCl$_3$, δ)
2.36 (2H, t, J = 6.0 Hz, —NHCH$_2$CH$_2$CO—), 3.03–3.74 (6H, m, —NHCH$_2$CH$_2$CONHCH$_2$CH$_2$S—), 5.04 (2H, s,

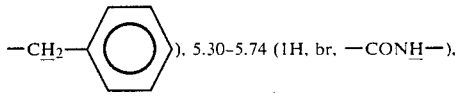 —CH$_2$—⟨❍⟩), 5.30–5.74 (1H, br, —CONH—), 6.09–6.67 (1H, br, —CONH—), 7.28 (5H, s.

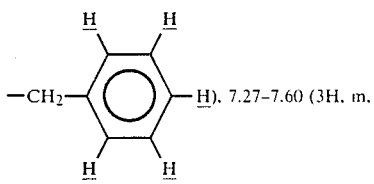 —CH$_2$—⟨❍⟩—H), 7.27–7.60 (3H, m,

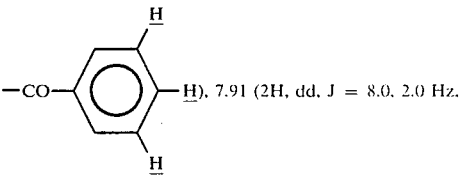 —CO—⟨❍⟩—H), 7.91 (2H, dd, J = 8.0, 2.0 Hz,

—CO—⟨❍⟩)

TLC Rf value(a): 0.33

EXAMPLE 4

N-(2-Acetylthioethyl)-3-(benzyloxycarbonylamino)-propionamide

To the stirred solution of 3-(benzyloxycarbonylamino)-N-(2-mercaptoethyl)propionamide (2 g) and triethylamine (0.8 g) in anhydrous THF (15 ml), acetyl chloride (0.6 g) is added dropwise under ice-water cooling. After the addition, the mixture is stirred for 30 minutes under ice-water cooling and additional 30 minutes at room temperature. The solution is filtered and the filtrate is concentrated in vacuo. The residue is dissolved in ethyl acetate (30 ml) and the solution is washed with saturated sodium bicarbonate solution, N hydrochloric acid and then saturated sodium chloride solution. The ethyl acetate solution is dried over anhydrous magnesium sulfate and concentrated in vacuo to give 1.6 g (70%) of the titled compound.
mp 83°–108° C. (benzene-cyclohexane)
IR (KBr, cm$^{-1}$): 3328, 3292, 1678, 1638, 1535, 1437, 1336, 1272, 1237, 1221, 1137, 1030, 730, 695, 625
NMR (CDCl$_3$, δ): 2.28 (3H, s, —SCOCH$_3$), 2.34–2.68 (2H, m, —NHCH$_2$CH$_2$CO—), 2.80–3.11 (2H, m, —NHCH$_2$CH$_2$S—), 3.18–3.68 (4H, m, —NHCH$_2$CH$_2$CONHCH$_2$CH$_2$S—), 5.04 (2H, s, —OCH$_2$C$_6$H$_5$), 5.28–5.84 (1H, br, —CONH—), 6.09–6.51 (1H, br, —CONH—), 7.24 (5H, s, —C$_6$H$_5$)
TLC Rf value(a): 0.27

EXAMPLE 5

3-(Benzyloxycarbonylamino)-N-(2-propionylthioethyl)-propionamide

By substituting propionyl chloride (0.72 g) for acetyl chloride in the procedure of Example 1, 1.9 g (79%) of the titled compound is obtained.

mp 77°-104° C. (benzene-cyclohexane)

IR (KBr, cm$^{-1}$): 3328, 3288, 1678, 1638, 1536, 1437, 1337, 1273, 1237, 1033, 944, 730, 693

NMR (CDCl$_3$, δ): 1.12 (3H, t, J=7.0 Hz, —S-COCH$_2$C$\underline{H}_3$), 2.34 (2H, t, J=6.0 Hz, —NHCH$_2$C$\underline{H}_2$CO—), 2.53 (2H, q, J=7.0 Hz, —SCOC$\underline{H}_2$CH$_3$), 2.77-3.14 (2H, m, —NHCH$_2$C$\underline{H}_2$S—), 3.14-3.67 (4H, m, —NHC$\underline{H}_2$CH$_2$CONHC$\underline{H}_2$CH$_2$S—), 5.03 (2H, s, —OC$\underline{H}_2$C$_6$H$_5$), 5.34-5.81 (1H, br, —CON$\underline{H}$—), 6.14-6.64 (1H, br, —CON$\underline{H}$—), 7.26 (5H, s, —C$_6\underline{H}_5$)

TLC Rf value$^{(a)}$: 0.34

EXAMPLE 6

3-(Benzyloxycarbonylamino)-N-(2-pivaloylthioethyl)-propionamide

By substituting pivaloyl chloride (0.94 g) for acetyl chloride in the procedure of Example 1, 1.8 g (69%) of the titled compound is obtained.

mp 87°-88° C. (ether-isopropyl ether)

IR (KBr, cm$^{-1}$): 3328, 3292, 1685, 1638, 1542, 1452, 1437, 1361, 1337, 1263, 1242, 1004, 947, 750, 697

NMR (CDCl$_3$, δ): 1.22 (9H, s, —SCOC(C$\underline{H}_3$), 2.33 (2H, t, J=6.0 Hz, —NHCH$_2$C$\underline{H}_2$CO—), 2.82-3.13 (2H, m, —NHCH$_2$C$\underline{H}_2$S—), 3.20-3.67 (4H, m, —NHC$\underline{H}_2$CH$_2$CON$\underline{H}$C$\underline{H}_2$CH$_2$S—), 5.04 (2H, s, —OC$\underline{H}_2$C$_6$H$_5$), 5.30-5.78 (1H, br, —CON$\underline{H}$—), 5.95-6.43 (1H, br, —CON$\underline{H}$—), 7.26 (5H, s, —C$_6\underline{H}_5$)

TLC Rf value$^{(a)}$: 0.39

EXAMPLE 7

3-(Benzyloxycarbonylamino)-N-[2-[diethylamino(thiocarbonyl)-thio]ethyl]propionamide To the solution of 3-(benzyloxycarbonylamino)-N-(2-bromoethyl)propionamide (10 g) in acetone (250 ml), sodium diethyldithiocarbamate trihydrate (6.8 g) in acetone (150 ml) is added and the mixture is stirred for 40 minutes at room temperature. The reaction mixture is filterd and the filtrate is concentrated in vacuo. The residue is dissolved in ethyl acetate (150 ml) and the solution is washed with N hydrochloric acid, N sodium hydroxide, water and saturated sodium chloride solution in the named order. The ethyl acetate solution is dried over anhydrous magnesium sulfate and concentrated in vacuo to give 10.7 g (89%) of the titled compound.

mp 90°-93° C. (benzene-hexane)

IR (KBr, cm$^{-1}$): 3325, 3296, 1685, 1635, 1537, 1488, 1413, 1267, 1240, 1201, 1143, 696

NMR (CDCl$_3$, δ): 1.24 (6H, t, J=7.0 Hz, —N(CH$_2$C$\underline{H}_3$)$_2$), 2.36 (2H, t, J=6.0 Hz, —NHCH$_2$C$\underline{H}_2$CO—), 3.17-4.20 (10H, m, —NHC$\underline{H}_2$C$\underline{H}_2$CONHC$\underline{H}_2$C$\underline{H}_2$S—CSN(C$\underline{H}_2$CH$_3$)$_2$), 5.04 (2H, s, —OC$\underline{H}_2$C$_6$H$_5$), 5.30-5.75 (1H, br, —CON$\underline{H}$—), 6.20-6.80 (1H, br, —CON$\underline{H}$—), 7.28 (5H, s, —C$_6\underline{H}_5$)

TLC Rf value$^{(a)}$: 0.40

What we claim is:

1. A compound of the formula [i] and salts thereof,

R$^1$—NHCH$_2$CH$_2$CONHCHCH$_2$S—R$^3$
　　　　　　　　　　　　　　|
　　　　　　　　　　　　　　R$^2$     [I]

wherein
R$^1$ is

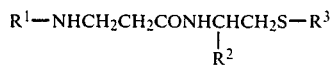

R$^2$ is hydrogen or carboxy;
R$^3$ is lower alkanoyl, (lower alkylamino)thiocarbonyl or

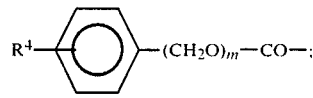

R$^4$ is hydrogen, lower alkyl or lower alkoxy; and
m and n, are the same or different, each is 0 or 1, said lower alkyl and lower alkoxy refer to groups having 1 to 6 carbon atoms, and lower alkanoyl refers to groups having 2 to 6 carbon atoms.

2. A compound as in claim 1 wherein R$^2$ is hydrogen.
3. A compound as in claim 1 wherein R$^4$ is hydrogen.
4. A compound as in claim 1 wherein R$^3$ is acetyl, propionyl or benzoyl.
5. 3-(Benzoylamino)-N-(2-benzoylthioethyl)propionamide as in claim 1.
6. N-(2-Acetylthioethyl)-3-(benzyloxycarbonylamino)propionamide as in claim 1.
7. 3-(Benzyloxycarbonylamino)-N-(2-propionylthioethyl)propionamide as in claim 1.
8. A pharmaceutical composition useful for the treatment of liver damage, comprising (i) a pharmaceutical carrier and (ii) a compound of the formula and pharmaceutically acceptable salts thereof in an amount sufficient for the treatment of liver damage, R$^5$—NHCH$_2$CH$_2$CONHCHCH$_2$S—R$^7$
　　　　　　　　　　　　　　|
　　　　　　　　　　　　　　R$^6$     [II]

wherein
R$^5$ is hydrogen, lower alkanoyl or

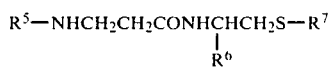

R$^6$ is hydrogen or carboxy;
R$^7$ is hydrogen, lower alkanoyl, (lower alkylamino)thiocarbonyl or

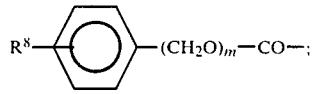

R$^8$ is hydrogen, lower alkyl or lower alkoxy; and m and n are the same or different, each is 0 to 1, said lower alkyl and lower alkoxy refer to groups having 1 to 6 carbon atoms, and lower alkanoyl refers to groups having 2 to 6 carbon atoms.

9. A composition as in claim 8 wherein the compound is 3-(benzyloxycarbonylamino)-N-(2-propionylthioethyl)propionamide.

10. A composition as in claim 8 wherein the compound is 3-benzoylamino-N-(2-benzoylthioethyl)propionamide.

11. A composition as in claim 8 wherein the compound is N-(2-acetylthioethyl)-3-(benzyloxycarbonylamino)propionamide.

12. A composition as in claim 8 wherein the compound is 3-amino-N-(2-mercaptoethyl)propionamide.

13. A composition as in claim 8 wherein the compound is 3-(benzyloxycarbonylamino)-N-(2-mercaptoethyl)propionamide.

14. A composition as in claim 8 wherein the compound is 3-acetylamino-N-(2-acetylthioethyl)propionamide.

15. A method for treatment of liver damage which comprises administering a composition as in claim 8.

* * * * *

UNITED STATES PATENT AND TRADEMARK OFFICE
CERTIFICATE OF CORRECTION

PATENT NO. : 4,552,765
DATED : November 12, 1985
INVENTOR(S) : Itaru MITA, et al It is certified that error appears in the above-identified patent and that said Letters Patent is hereby corrected as shown below:

Column 1, lines 5 and 6, change "re-ferrs" to --referred--.

Column 1, line 57, change "differnt" to --different--.

Column 3, line 22, change "namly" to --namely--.

Column 6, line 11, change "magensium" to --magnesium--.

Column 8, line 1, "IR(KBr,cm$^{31}$)" should be --IR(KBr,cm$^{-1}$)--.

Column 9, line 48, change "filterd" to --filtered--.

Column 9, last line, change "[i]" to --[I]--.

Column 10, line 41, after "formula" insert --[II]--.

Signed and Sealed this

Eighteenth Day of November, 1986

*Attest:*

DONALD J. QUIGG

*Attesting Officer*     *Commissioner of Patents and Trademarks*